United States Patent

Wolverton et al.

Patent Number: 5,351,438
Date of Patent: Oct. 4, 1994

[54] PLANTER CONTAINER FOR INDOOR AIR PURIFICATION

[76] Inventors: Billy C. Wolverton, 514 Pine Grove Rd.; John D. Wolverton, P.O. Box 411, both of Picayune, Miss. 39466

[21] Appl. No.: 72,835

[22] Filed: Jun. 7, 1993

Related U.S. Application Data

[63] Continuation-in-part of Ser. No. 832,479, Feb. 7, 1992, Pat. No. 5,217,696.

[51] Int. Cl.$^5$ .............................................. A01G 25/06
[52] U.S. Cl. ............................................. 47/79; 47/80; 47/81; 422/120
[58] Field of Search ................. 47/79, 79 I, 80, 81; 220/506, 469, 466, 488, 495, 565; 422/120

[56] References Cited

U.S. PATENT DOCUMENTS

| | | | |
|---|---|---|---|
| D. 255,555 | 6/1980 | Smith | 47/79 X |
| 2,387,340 | 10/1945 | Moriarty | 47/79 |
| 3,137,096 | 6/1964 | Hopkins | 47/79 |
| 3,334,440 | 8/1967 | Choquette | 47/79 |
| 4,236,351 | 12/1980 | Smith | 47/79 |

FOREIGN PATENT DOCUMENTS 2316275  10/1974  Fed. Rep. of Germany ....... 47/79 I

*Primary Examiner*—Robert J. Warden
*Assistant Examiner*—Amalia Santiago
*Attorney, Agent, or Firm*—Alexander Norcross

[57] ABSTRACT

A planter container for growing a house plant in soil or a growth medium which contains multiple vent pipes extending vertically from the bottom to the top of the container. Air convection occasioned by the natural water transpiration processes of the growing plant is sufficient to cause polluted air flow through the vent pipes, and the vent pipes then enhance air flow throughout the root growth medium, exposing the air to large surface areas of plant root and biologically active growth medium for enhanced microorganism removal of volatile organic chemicals.

4 Claims, 1 Drawing Sheet

PLANTER CONTAINER FOR INDOOR AIR PURIFICATION

BACKGROUND OF THE INVENTION

This Application is a continuation in part of my co-pending application Ser. No. 07/832,479 filed Feb. 7, 1992, now issued as U.S. Pat. No. 5,217,696 on Jun. 8, 1993, which is incorporated in full herein.

This Invention relates to apparatus for biological purification of Air contaminants, especially through the use of naturally occurring house plants, and microbial species which naturally occur in symbiotic relation to the roots of such plants.

More than ten years of research have shown that common houseplants can remove volatile organic chemicals from air inside sealed chambers. Microbe cultures occurring naturally on and around plant roots, and existing symbiotically with such plants, have been identified as the major mechanism involved in the chemical degradation and elimination of such organic chemicals. Because each species of plant cultures different types and numbers of microbes on and around their roots, some plants are more effective than others in the removal of toxic chemicals from the air.

Typical such chemical contaminants, many of which occur naturally in building atmospheres, or as the result of the wide spread use of plastics and chemicals in constructing, painting and preserving modern buildings are formaldehyde, xylene, ammonia and benzene. The ability of more than forty different houseplants to remove such chemicals has been determined and reported in Wolverton, et al, Economic botany, 3(22):24–228(1984); Wolverton, B. C. and John D. Wolverton, Proceedings Intl. Conf. on life Support and Biospherics, Univ. of Alabama in Huntsville, 117–1226 (1992); Wolverton, B. C. and John D. Wolverton, Plants and soil microorganisms for removal of xylene, formaldehyde, and ammonia from indoor environment, Journal Mississippi Academy of Sciences, Vol 38 (1993).

The removal of such contaminants depends on the air borne contaminant being brought in contact with the live microorganisms under conditions where the microorganisms can react with and degrade the toxic gases. Since these microorganisms are within soils or plant growth media, within which the plant root structure is imbedded for nutrition and growth, this translates into the problem of increasing the surface exposure of such biologically active soils to the contaminated air.

My co-pending application describes various prior art devices for increasing the exposure of plant root soil to air flow, for example Saceman, U.S. Pat. No. 4,975,251. The invention of my co-pending application describes a structure in which a light or similar heat source, within a chimney, builds convective air flow which flows air up through perforated tubes buried in the soil.

SUMMARY OF THE INVENTION

This invention describes a planter container for growing a house plant in soil or a growth medium which contains multiple vent pipes extending vertically from the bottom to the top of the container. Air convection occasioned by the natural water transpiration processes of the growing plant is sufficient to cause polluted air flow through the vent pipes, and the vent pipes then enhance air flow throughout the root growth medium, exposing the air to large surface areas of plant root and biologically active growth medium for enhanced microorganism removal of volatile organic chemicals.

The apparatus comprises a house plant container having multiple air intake or vent tubes surrounding the inner surface of the container. The lower section of each such tube is solid; the upper section is perforated for maximum flow of air into the surrounding microbially enriched growth medium.

The container contains a water feed tube for insuring a supply of water to the growth medium within the container. The solid portion of the vent tubes defines a lower depth of the container for holding water to insure adequate moisture levels for the growth medium or soil. A water level indicator insures that neither too much nor too little water level exists; such a level indication can be a tube with float and indicator as described in my co-pending application.

Air movement through the vent tubes occurs because of convection currents created by plant leaves during evapo-transpiration. Cool air, created when the leaves add water vapor into the room, creates a small temperature difference between the bottom of the pot and the area surrounding the leaves, causing slow air movement up through the vent tubes. This air movement flows through the perforated section of the vent tubes into the moist, biologically active growth medium, significantly increasing the active microorganism cleaning of the air, without requiring the use of blowers or active fans to force the air through the growth medium.

DETAILED DESCRIPTION OF THE INVENTION

Figure 1:
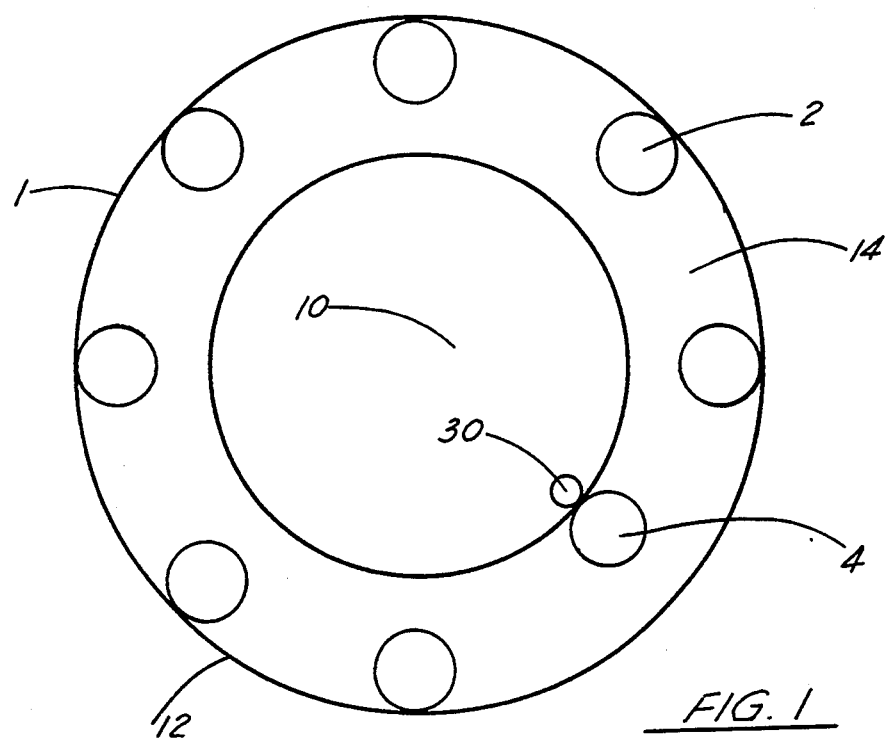
FIG. 1 is a top view of the container of the invention.
Figure 2:
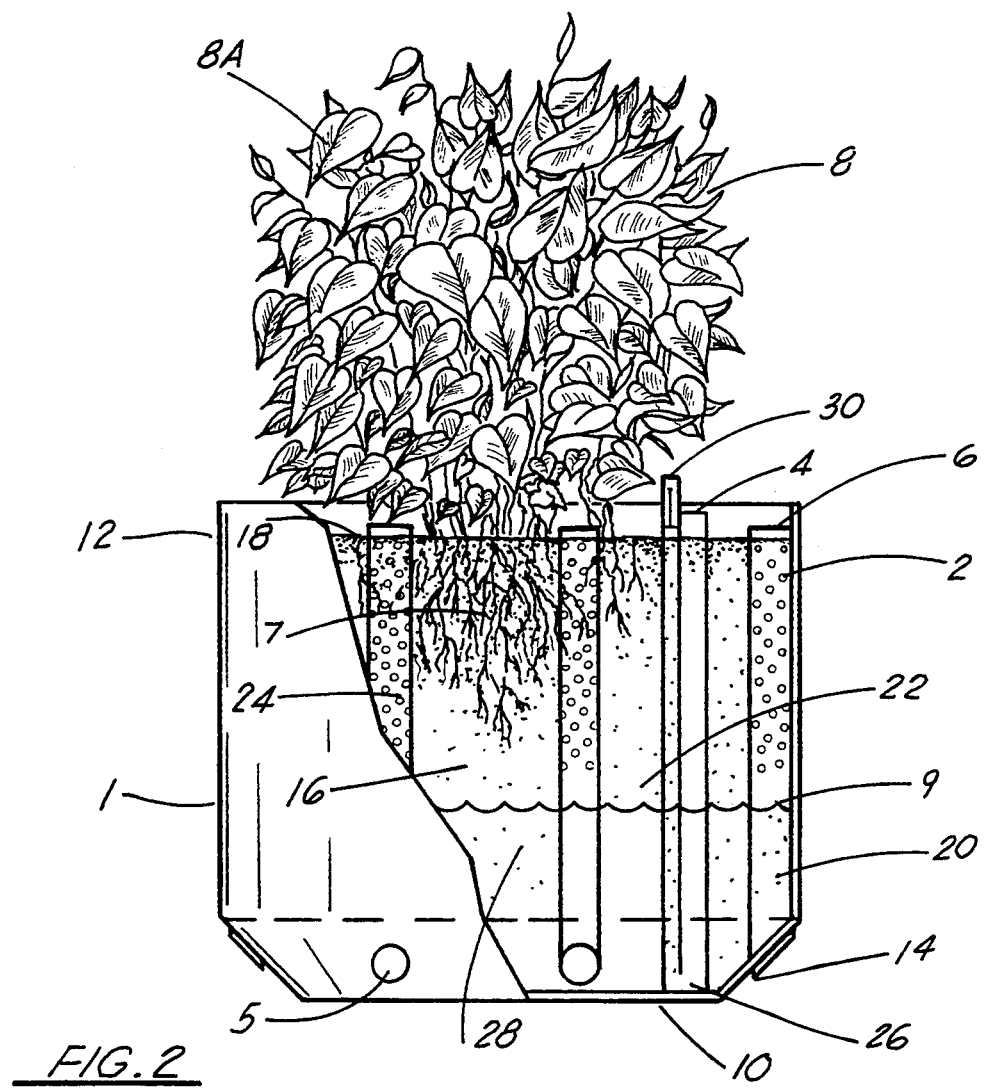
FIG. 2 a side view, with cut away section, of the invention with a plant, the plant root system being embedded in a growth medium.

The invention is shown in FIG. 2 as a container 1 for a house plant 8. As typical for house plant containers 1, the container 1 has a closed base 10 and vertically arising walls 12, the walls 12 and the base 10 being joined along a bottom tapered edge 14 to form a closed water tight container 1 for holding a plant growth medium 16, which may range from a potting soil or mixture of granular particles and composted organic materials to an undifferentiated soil.

Within the growth medium 16 is planted a house plant 8, which grows and is sustained by its root structure 7. Such a root structure 7, within a growth medium 16 is biologically active due to naturally occurring microorganisms, which grow and exist in symbiotic relationship with the plant roots. These microorganisms are an essential part of the plant's ability to extract nutrients form the growth medium 16, and thus, so long as the plant is healthy, the growth medium 16 and root structure 7 is biologically active.

The metabolic processes involved require water both to support the microorganisms and to transport the dissolved nutrients form the growth medium to the plant's roots. The level of water is critical; if the growth medium dries out, the microorganisms die together with the plant. If the soil becomes fully water saturated, no air can pass through the growth medium, and, for many house plants, the roots will ultimately rot. For each house plant in a container, therefore, there is an optimum water level 9, which insures adequate moisture for plant growth, but not excessive water. The water from this water level 9 migrates throughout the growth medium 16 by diffusion or capillary attraction, thus insuring an optimum moisture coating for all particles of growth medium, However, the growth medium is exposed to air above water level 9.

It has been found, as discussed in the background of the invention above, that the microorganisms associated with the root structure 7 also are highly effective in reducing and removing various volatile organic contaminants in the air. This process is a natural one, related to the action of these microorganisms in extracting nutrients from the air for the plant's root structure 7. The efficiency of this process depends on the quantity of air which is exposed to the microorganisms. Since the process of plant growth results in the desired microorganisms spreading throughout the growth medium 16, this translates into a requirement to pass as large a quantity of air through the growth medium 16 as possible, consistent with the requirement that the growth medium not be dried out.

The invention 1 is a container which provides for enhanced air transport to and through the growth medium 16 by natural convective processes, without requiring fans, powered mechanical ventilation apparatus or the use of externally generated heat to created convective air flow.

The inventive container 1 is provided with a plurality of air vent tubes 2 or air flow pipes 2 which extend through the bottom edge 14 of the container 1 vertically upward to an open top 6 above the upper level 18 of the growth medium. Air vent tubes 2 are open at their top 6 and at the bottoms 5 thereof where they sealingly pass through the bottom 14 of the container 1. Each vent tube 2 has a lower section 20 which is a closed surface. This closed surface lower section 20 extends upward to an intermediate level 22, and then the tube 2 changes to an upper section 24 which is a porous or foraminous surface, for ready flow of air into the growth medium 16.

The vent tube 2 lower section 20, together with the container 1, forms an enclosed sealed container for holding water in contact with the growth medium 16. This water should be held at a preferred water level 9 below the intermediate level 22. For this purpose, a vertical watering tube 4 is set into the container extending from a point above the upper level 18 of the growth medium 16, and extending downward to a lower opening 26 for replenishment flow of water 28 into the bottom of container 1.

Since the level 9 of the water 28 is not ordinarily visible, unless a transparent container 1 is used, a water level indicator 30 is provided, preferably adjacent the watering tube 4, to indicate the level 9 of water within the container 1. Such an indicator is shown in my co-pending application, and is incorporated here as if fully set forth. Many other indicators will suggest themselves to skilled worker in the field, and there are many variations of the idea of a float driving an externally visible indicator, or a sight glass for indicating water level.

The supply of water 28 maintains the growth medium 16 and root structure 7 in a moist state, but not saturated, Therefore the growth medium will be a moist porous material, each grain or particle having a moist covering which will be active with microorganisms, but the grains separated by small spaces so that air can permeate throughout the growth medium 16 and root structure 7. The natural temperature differences created by the evaporation of water form the leaves of the plant 8 will create a convective flow between the level of the plant's leaves 8A and the bottom 10 of the container, causing convective air flow through the open ended vent tubes 2. This air flow through the vent tubes 2 will in turn cause vortices and pressure differentials along and across the perforated upper section 24 of the vent tubes 2, enhancing air flow and interchange throughout the growth medium 16 and root structure 7.

Thus by use of the inventive container 1, the natural flow of air into and through the houseplant's 8 root structure 7 and biologically active root growth medium 16 is enhanced, and the known ability of the symbiotically associated naturally occurring microorganism to cleanse the air is significantly enhanced.

It will be clear to those skilled in the art how the form of the container may be modified, as is common to produce decorative containers; the form of the vent tubes may likewise be varied to suit the container shape. The invention therefore extends beyond the cylindrical container shown as an exemplar to all plant containers having essentially vertically arising vent tubes embedded in the soil for enhancing the interchange of air through the particulate moist soil, as claimed.

We claim:

1. An apparatus for planting a houseplant comprising:
   a container defining an interior soil containing space, defined by a perforated base and a surrounding wall rising to a top level;
   a plurality of vertical vent tubes upwardly extending from said base up to, and terminating at, said top level, said tubes being open through said base, and open at said top level;
   said vent tubes being imperforate and sealingly enclosed from said base to an intermediate level;
   said vent tubes being perforated from said intermediate level to said top level.

2. The apparatus of claim 1, further comprising:
   said intermediate level defining a level a water within said container;
   a vertical watering tube extending form said top level to said base, an opening in said watering tube between said intermediate level and said base for the passage of water from said watering tube to the interior of said container.

3. The apparatus of claim 2 further comprising:
   means for indicating the level of water within said container.

4. The apparatus of claim 2 further comprising a water indicator tube positioned within said container, projecting above the container to a distal end, said tube formed of a transparent material;
   a float slidably mounted within said water indicator tube;
   a rod and indicator extending upwardly form said float;
   a series of indicia extending downwardly from the distal end of the water indicator tube, cooperative with said indicator tube for indicating the position of the float within said container.

* * * * *